United States Patent [19]

Havira et al.

[11] Patent Number: 5,578,758
[45] Date of Patent: * Nov. 26, 1996

[54] RAIL INVESTIGATING ULTRASONIC TRANSDUCER

[75] Inventors: R. Mark Havira, New Fairfield; Anthony Iorfino, Stamford, both of Conn.

[73] Assignee: Pandrol Jackson Technologies, Inc., Danbury, Conn.

[*] Notice: The term of this patent shall not extend beyond the expiration date of Pat. No. 5,419,196.

[21] Appl. No.: 492,986

[22] Filed: Jun. 21, 1995

[51] Int. Cl.$^6$ ................................. G01N 29/04
[52] U.S. Cl. ................................. 73/636; 73/642
[58] Field of Search .................... 73/598, 600, 636, 73/642, 635, 638, 639; 367/13, 150, 165, 166, 171, 173

[56] References Cited

U.S. PATENT DOCUMENTS 4,557,146  10/1985  Buffington ........................... 73/642
4,576,048  3/1986   Glenn ................................... 73/642
5,056,368  10/1991  Kawasaki ............................. 73/642

*Primary Examiner*—Christine K. Oda
*Attorney, Agent, or Firm*—St. Onge Steward Johnston & Reens

[57] ABSTRACT

An ultrasonic railhead investigating apparatus is described wherein a side looking transducer is used with a lens to focus the beam in a manner whereby rail defects in the sides of rail head are more readily detected. In one form of the invention a side rail investigating transducer is provided with a curved emitting surface and so located as to place the focused acoustic beam between a side of the rail and the rail center. The curved emitting surface can be part of a cylindrical surface aligned parallel with the longitudinal axis of the rail or a spherically shaped emitting surface to provide a conically shaped beam for investigating the side of a rail.

6 Claims, 3 Drawing Sheets

RAIL INVESTIGATING ULTRASONIC TRANSDUCER

FIELD OF THE INVENTION

This invention generally relates to ultrasonic transducers for the investigation of rails and more specifically to ultrasonic transducers for investigating the sides of webs and rail heads.

BACKGROUND OF THE INVENTION

Ultrasonic investigation of rails is well known. For example U.S. Pat. No. 4,165,648 describes a wheel assembly, which is adapted to ride on top of a rail and contains a plurality of ultrasonic transducers for investigating different parts of a rail. A pair of transducers are oriented to investigate the rail along opposite longitudinal directions, another transducer is oriented to vertically investigate the web of the rail and a fourth transducer is intended as a side-looker with which side portions of the rail head are to be laterally investigated.

The side-looker is mounted on a yoke assembly, near the axis and is positioned off to one side to investigate an opposite side of the rail head. The transducer produces a beam intended to have a 40 degree angle relative to the normal to the rail surface inside the rail head so that the beam will intersect one of the lower corners of the head. Although this transducer can be effective for detecting vertically split rail heads it does not accommodate the effect of the curvature of the rail head and the head wear that one encounters under field conditions.

The curvature of the rail head causes a variety of angles of both compressional and shear components to be present inside the rail head and thus creates difficulties in interpreting the resulting signals detected at the transducer. For example, if the resultant angle is to be 40 degrees inside the head for a compressional wave, then a 20 degree shear wave will also be present. Since a mode conversion is relied upon to accomplish the resultant angle in the rail head, there is but a limited range of incident angles available inside the wheel. This limitation arises from the use of essentially a common exit point for all of the transducers mounted inside the wheel and the resulting need to avoid interference with the other transducers by internal wheel reflections from the side-looking transducer.

The '648 patent illustrates that for one particular beam direction, the corners of one rail head and its proportionately smaller sizes are likely to be intersected by a 40 degree beam. However, when the rail head undergoes significant wear on its upper surface, as is often the case, the beam will miss the lower corner. Instead the beam is likely to strike an inner surface near the web, which scatters the beam inside the head, and fails to provide the type of return needed to detect vertical flaws near the side of the rail head.

In our patent entitled Ultrasonic Side-Looker For Rail Head Flaw Detection, filed on Mar. 19, 1993 bearing Ser. No. 08/034,420, U.S. Pat. No. 5,419,196, and owned by the same Assignee as of this invention, a side looking ultrasonic transducer is described with which a sufficiently wide and properly angled beam within the head of a rail is achieved for the detection of flaws such as vertical cracks extending longitudinally along the rail.

Excessive wear of a rail head can occur so that the top rail surface becomes so distorted that the detection of flaws in the side of the rail head is obscured by reflections from other parts of the rail such as the fillet region. The returns are then more difficult to process with reliable detection of flaws.

SUMMARY OF THE INVENTION

With a rail investigating apparatus in accordance with the invention a beam from an ultrasonic transducer is focused in a particular manner so as to avoid reflections from rail side surfaces and enhance the detectability of flaws such as vertical cracks in badly worn sides of the head of the rail.

This is achieved in accordance with one embodiment of the invention by employing an ultrasonic transducer whose acoustic beam emitting surface is provided with an acoustic lens that enables the transducer to bring the acoustic beam to a focus within a rail head. The lens focuses the beam sufficiently so as to avoid its impact on undesired rail surfaces while having sufficient spread to investigate rail regions of interest.

In one form of the invention a side-looking ultrasonic transducer is provided with a concave acoustic beam emitting surface which focuses the beam. The transducer is so located that its beam passes through of a flexible membrane retaining fluid in a wheel rotating over the running surface of a rail and is refracted towards a side of the rail head. The focal point of the beam is located between the center of the rail and a side surface of the head so as to avoid impacting of the beam on a fillet region of the rail while illuminating the side of the rail head so as to produce reflections from flaws such as vertical cracks extending along the rail.

In another form of the invention an ultrasonic transducer having a an acoustic focusing lens is placed so as to direct a focused acoustic beam into the web of a rail and avoid reflections from the side surfaces of the web. This enables a faster investigation of the rail while reducing false flaw detections.

It is, therefore, an object of the invention to provide an improved ultrasonic apparatus for detecting flaws in a rail even in the presence of severe rail head wear and distortions. It is a further object of the invention to provide an apparatus for ultrasonically investigating the side of a rail head with reduced interference from reflections by nearby surfaces such as the fillet region of the rail.

These and other objects and advantages of the invention will be understood from the following detailed description of several embodiments as shown in the drawings.

DETAILED DESCRIPTION OF THE DRAWINGS

Figure 1:
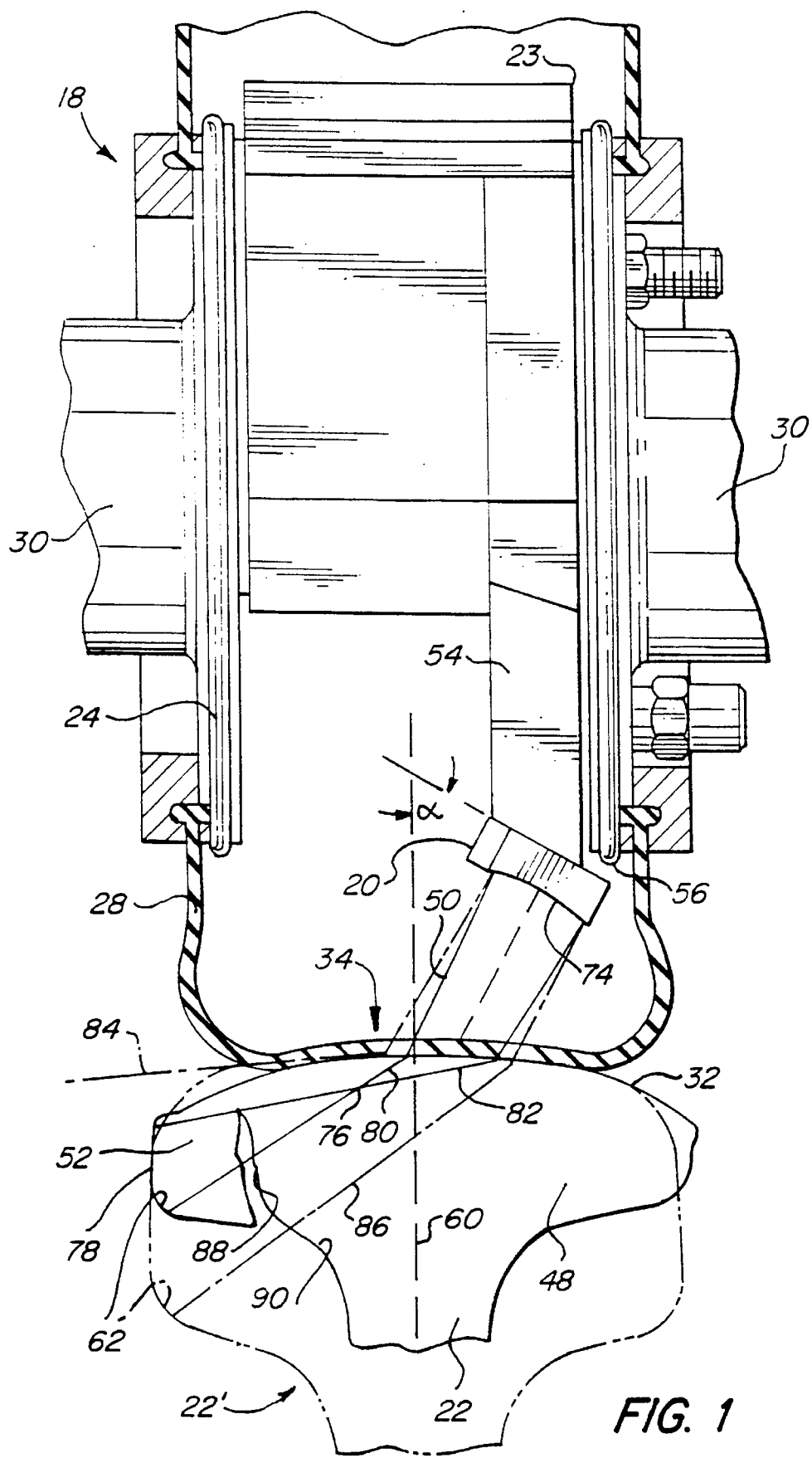
FIG. 1 is a front sectional view of an ultrasonic apparatus for investigating a rail in accordance with the invention; .
Figure 2:
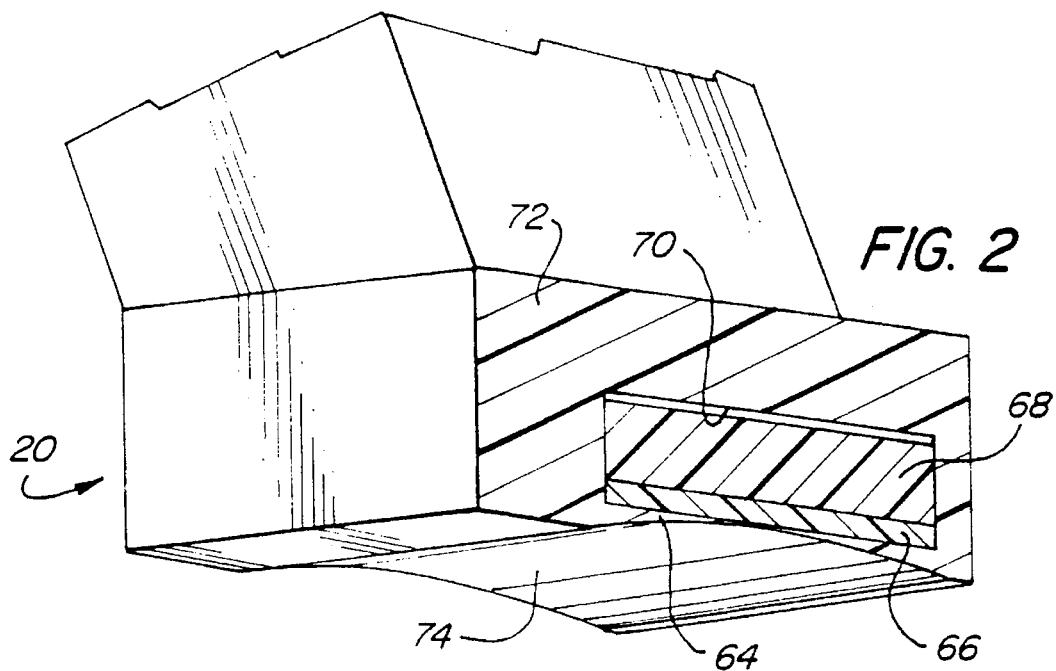
FIG. 2 is an enlarged perspective sectional view of an ultrasonic transducer used in the apparatus of the invention.

With reference to FIGS. 1 and 2 a wheel-type ultra-sonic investigation apparatus 18 for ultrasonic inspection of a rail 22 is shown. The apparatus 18 is part of a flaw detection system (not shown) that is mounted on a carriage and includes suitable electronic signal processing equipment to analyze the return signals detected by ultrasonic transducers such as 20 that is mounted to a yoke 23 inside a rotating fluid-filled wheel 24. The yoke 23 and wheel 24 can be made in the manner as shown and described in our above mentioned patent. This patent is incorporated herein by reference thereto.

The wheel 24 is rotationally mounted to a support of the carriage which is not shown. Typically, four wheels 24 are used, two for each rail 22. Each wheel 24 is filled with a fluid mixture of glycol and water to improve the ultrasonic coupling through the flexible outer membrane 28. The yoke 23 is affixed to twin axially-aligned but spaced-apart shafts, not shown, in alignment with wheel flanges 30. The yoke 23 is held in a fixed stable position as illustrated while the wheel 24 rotates as it travels along the top surface 32 of rail 22. Suitable downward pressure is applied to the wheel 24 to produce an area spot 34 in membrane 28 for appropriate ultrasonic transmission into and out of the rail 22.

Transducer 20 is a side-looking transducer and is mounted well below the apex of yoke 23 and to its side. Transducer 20 produces an ultrasonic beam 50 that is also incident on area 34, but in a lateral direction to investigate the side 52 of rail head 48. The transducer 20 operates in both a transmit and receive mode.

The side-looking transducer 20 is mounted to yoke 23 by way of a removable extension bracket 54. Alternately, yoke 23 can be formed so as to have an extension 54 become an integral part. As illustrated in the view of FIG. 1 the side-looker 20 is suspended to just below an adjacent side flange 56, to a region that is near the flat portion 34 of the flexible outer wheel membrane 28, but not so close as to be interfered with from wheel vibration or bouncing effects attributable to irregularities encountered along the running top surface 32 of rail 22. If the side-looking transducer 20 is mounted on a yoke in a separate wheel, which may be wider and/or larger, the side-looker can be located anywhere along beam 50.

The side-looker 20 further is inclined relative to the central vertical 60 to rail 22 to form an angle, alpha. The angle alpha is selected so as to provide an optimum beam inside rail 22 for inspection of side 52 and assure that at least a portion of the beam 50 will intersect the lower corner 62 of rail head 48. The side-looker 20 further is so sized as to produce a sufficient beam width within the rail head 48 preferably to assure intersection of lower side corner 62 even when a substantial amount of the upper part of the rail head 48 has been worn away as illustrated in FIG. 1. The angle alpha can be in the range from about 61° to about 65° within the fluid inside the wheel membrane 28 so as to produce a beam angle within the rail head 48 in the range from about 45° to about 75° with a beam cross-sectional size of the order of about 0.5 inches square.

As illustrated in FIGS. 1 and 2 the side-looker transducer 20 produces a focused acoustic beam 50 by employing a lens 64 in front of the acoustic beam generating element 66. Alternatively the lens can be made by shaping the emitting surface of a piezoelectric element into a similarly curved surface. The term lens as employed herein, therefore encompasses both either a shaped material as illustrated in the drawings at 64 or a similar shaping of the emitting surface of the element 66. An acoustic absorber material 68 is used behind the element 66. The element 66, and the absorber 68 are mounted within a cavity 70 formed inside a housing 72 made of an appropriate material such as epoxy, which is cast around the element 66 and the absorber 68.

The lens 64 is formed by casting or grinding away the portion of the housing 72 that is located in front of the element 66. Either process leaves a concave emitting surface 74. The emitting surface 74 has a concavity that is shaped to conform along a cylinder having a radius R of predetermined size and an axis located parallel to the longitudinal dimension of the rail 22. The radius R is selected so that the refracted acoustic focus 76 is located inside the rail head 48 and between the center line 60 and a side surface 78. The acoustic focus 76 is a line of a length commensurate with the length of the lens 64 and is located within the rail head 48 parallel to the longitudinal dimension of the rail 22.

Alternatively the emitting surface 74 can be spherically or parabolically shaped to form a correspondingly focused conically shaped beam inside the rail head 48.

The preferred location of the focal point is just after the entry of the beam 50 into the steel of the rail 22. This provides, within the steel rail head 48, an acoustic beam whose energy is primarily contained within the solid lines 80, 82 representing the approximate 3 db points for the beam. The dashed lines 84, 86 represent lower, 10 db down, energy levels of the ultrasonic beam emitted by the transducer 20. The overall effect of the focused beam inside rail head 48 is a substantially cleaner return reflection from a vertical flaw such as 88 with little energy being returned from the fillet region 90 in rail 22.

The radius of curvature of the beam emitting surface 74 and the acoustic focal length of the beam 50 are not the same. Typically the focal length is somewhat longer due to the acoustic travel time through the various materials. In one embodiment of the invention the radius of curvature for transducer 20, sized and mounted in the manner as described herein and the aforementioned patent was 3.125 inches and the fluid focal length was 3.85 inches. This configuration yielded satisfactory acoustic returns from a flaw in a rail head 48 that was as badly worn and distorted as shown in FIG. 1.

Figure 3:
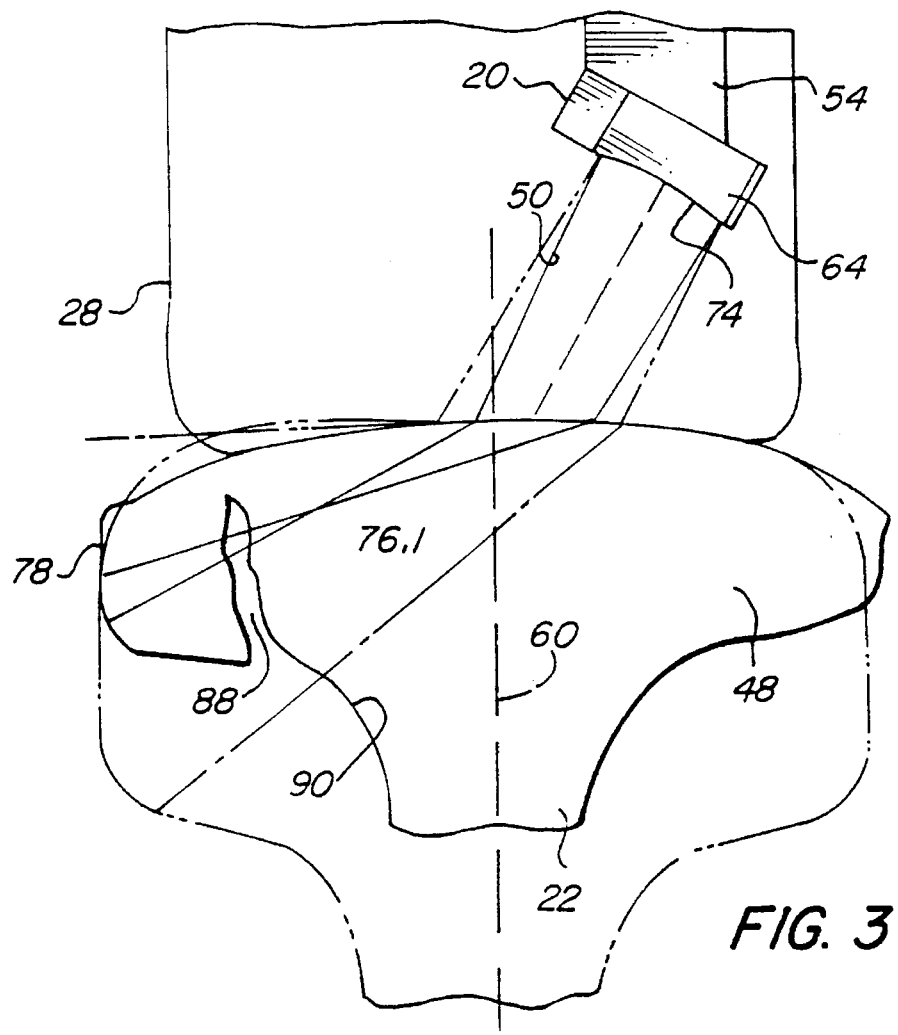
FIG. 3 is a partial front section view as in FIG. 1 but with a different focal length ultrasonic transducer.

When the radius of curvature of the lens 64 is lengthened, say to 3.75 inches and maintaining other transducer configurations the same, then the acoustic focal point 76.1 is moved, as shown in FIG. 3, away from the center line 60 towards the side surface 78. At the same time more energy is returned from the fillet region 90 so as to reduce the clarity of the acoustic return signals.

Hence, the radius of curvature for the lens 64 and its associated acoustic focal length and the location and size of the transducer are all selected to provide a focused beam of limited width within the rail head 48. The focal point is located so as to enable the detection of vertical flaws in the side of the rail head with reduced reflections from the adjoining fillet region.

Figure 4:
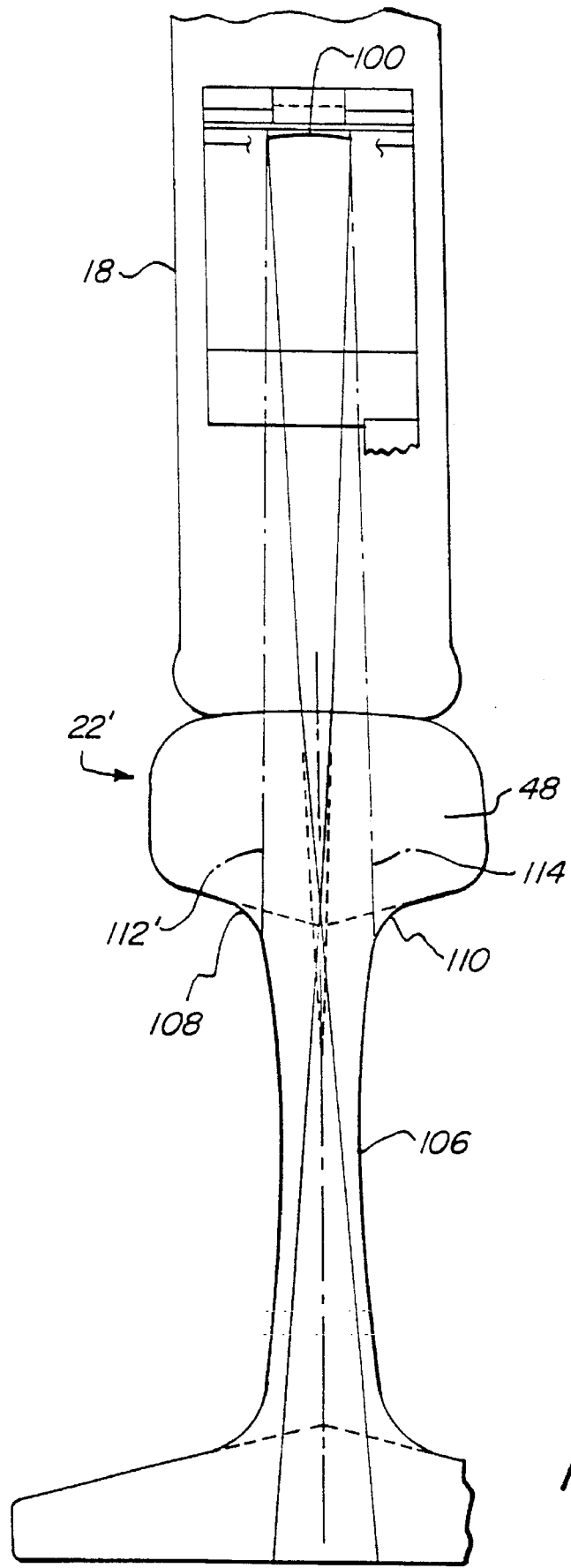
FIG. 4 is a front section view of a rail web investigating apparatus in accordance with the invention.

FIG. 4 illustrates use of a focused ultrasonic transducer 100 on yoke 102 in an ultrasonic rail investigating wheel 18. Transducer 100 is used as the "0°" transducer for investigating the web 106 of rail 22'. Since only the low energy portions of the beam, as suggested by the 10 db down beam lines 112, 114, are likely to be incident upon the fillet regions spurious echoes from fillet regions 108, 110 and the bottom of the rail head 48 are substantially reduced.

In order to attain a focus beam as shown in FIG. 4 a substantially larger than usual transducer is required, of the order of about 1.5 inches diameter. Use of such transducer would require adapting yoke 102 to accommodate the larger transducer 100.

Having thus described several embodiments of the invention its advantages can be appreciated. Variations from the drawings and description can be made by one skilled in the art without departing from the scope of the invention as determined by the following claims.

What is claimed is:

1. An apparatus for an acoustic investigation of a rail with a fluid filled rotating wheel inside of which is a stable yoke on which a plurality of ultrasonic transducers are mounted for the investigation with ultrasonic beams which exit the wheel at a generally common area in a flexible outer membrane of the wheel as it rotates about an axis to travel along the top running surface of the head of the rail under inspection, comprising:

an ultrasonic transducer mounted to the yoke, below the rotational axis of the wheel and away from ultrasonic beams from other transducers, and having a single, discrete area, focused beam emitting surface with a radius of curvature selected so that the focal point of the ultrasonic beam, after acoustic refraction, is located between the center of the rail and an outer lateral surface of the rail head, said focused beam emitting surface further being so located and sized so as to direct the ultrasonic focused beam at the common area of the flexible outer membrane to enter the rail head in a direction that significantly reduces reflections from outer rail surfaces below the acoustically refracted focal point of the ultrasonic beam inside the rail.

2. The apparatus as claimed in claim 1 wherein the radius of curvature is selected so as to provide an acoustic beam focal length of about 3.85 inches as determined for the fluid inside the wheel.

3. The apparatus as claimed in claim 1 wherein the focused beam emitting surface is shaped along a section of a cylindrical surface, said cylindrical surface having a center axis, and with said ultrasonic transducer being aligned so as to place the center axis generally parallel with the longitudinal dimension of the rail.

4. The apparatus as claimed in claim 1 wherein the rail has a center web which joins the rail head at fillet regions, and wherein the ultrasonic transducer is further so located and sized as to form, within the rail head, an acoustic beam which substantially avoids impacting on a fillet region.

5. The apparatus as claimed in claim 1 wherein the rail has a center web and wherein the ultrasonic transducer is so mounted to the yoke and so sized as to place and fit the focal point of the acoustic beam within the web of the rail with substantially reduced reflections from fillet surfaces of the rail.

6. In an apparatus for an acoustic investigation of a rail with a fluid filled rotating wheel inside of which is a stable yoke on which a plurality of ultrasonic transducers are mounted for the investigation of the rail with ultrasonic beams that exit at a generally common flat area formed in a flexible outer membrane of the wheel as it rotates about an axis to travel along the top running surface of the rail head of the rail under inspection and wherein the beams have different angles relative to the normal to the top running surface to investigate forward, backward and downward regions of the rail, the improvement comprising:

an ultrasonic side-looking transducer mounted to the yoke and located in the vicinity of the generally common flat area below and on a side of the yoke, said side-looking transducer being oriented so as to produce an ultrasonic beam within the wheel fluid that is directed at the generally common flat area with a fluid angle within a range from about 61 degrees to about 65.5 degrees relative to a normal to the top surface of the rail, with the normal located in a plane which is transverse to the rotational axis of the wheel, said side-looking transducer having an acoustic beam emitting surface with a concave curvature selected to place the acoustically refracted focal point of the beam between the center of the rail and a side thereof;

and wherein the beam inside the rail head has a head angle relative to the normal in the range from about 45 degrees to about 75 degrees as measured within a plane that is generally transverse to the top running surface of the rail, said beam further having a width selected to produce, within the rail head, an ultrasonic beam, at least a portion of which remains incident on a lower corner thereof independent of the presence of significant rail head wear and produces reflections from the lower corner with reduced reflections from a nearby fillet region; said reflections or an absence thereof being able to indicate the presence of vertical rail head flaws which run generally along the rail.

* * * * *